(12) United States Patent
Song et al.

(10) Patent No.: US 7,964,340 B2
(45) Date of Patent: Jun. 21, 2011

(54) ONE-STEP ENZYMATIC AND AMINE DETECTION TECHNIQUE

(75) Inventors: Xuedong Song, Roswell, GA (US); RameshBabu Boga, Alpharetta, GA (US); Chibueze Obi Chidebelu-Eze, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 242 days.

(21) Appl. No.: 12/426,973

(22) Filed: Apr. 21, 2009

(65) Prior Publication Data

US 2009/0226938 A1      Sep. 10, 2009

Related U.S. Application Data

(62) Division of application No. 10/881,010, filed on Jun. 30, 2004, now Pat. No. 7,521,226.

(51) Int. Cl.
*C12Q 1/00* (2006.01)

(52) U.S. Cl. ......................................... 435/4

(58) Field of Classification Search .................. None
See application file for complete search history.

(56) References Cited

U.S. PATENT DOCUMENTS

| | | | |
|---|---|---|---|
| 4,094,647 A | 6/1978 | Deutsch et al. |
| 4,110,529 A | 8/1978 | Stoy |
| 4,168,146 A | 9/1979 | Grubb et al. |
| RE30,267 E | 5/1980 | Bruschi |
| 4,210,723 A | 7/1980 | Dorman et al. |
| 4,275,149 A | 6/1981 | Litman et al. |
| 4,363,874 A | 12/1982 | Greenquist |
| 4,366,241 A | 12/1982 | Tom et al. |
| 4,374,925 A | 2/1983 | Litman et al. |
| 4,385,126 A | 5/1983 | Chen et al. |
| 4,426,451 A | 1/1984 | Columbus |
| 4,435,504 A | 3/1984 | Zuk et al. |
| 4,441,373 A | 4/1984 | White |
| 4,442,204 A | 4/1984 | Greenquist et al. |
| 4,444,592 A | 4/1984 | Ludwig |
| 4,477,635 A | 10/1984 | Mitra |
| 4,480,042 A | 10/1984 | Craig et al. |
| 4,533,499 A | 8/1985 | Clark et al. |
| 4,533,629 A | 8/1985 | Litman et al. |
| 4,537,861 A | 8/1985 | Elings et al. |
| 4,540,659 A | 9/1985 | Litman et al. |
| 4,562,157 A | 12/1985 | Lowe et al. |
| 4,595,661 A | 6/1986 | Cragle et al. |
| 4,596,697 A | 6/1986 | Ballato |
| 4,703,017 A | 10/1987 | Campbell et al. |
| 4,722,889 A | 2/1988 | Lee et al. |
| 4,727,019 A | 2/1988 | Valkirs et al. |
| 4,743,542 A | 5/1988 | Graham, Jr. et al. |
| 4,748,116 A | 5/1988 | Simonsson et al. |
| 4,776,944 A | 10/1988 | Janata et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,849,338 A | 7/1989 | Litman et al. |
| 4,855,240 A | 8/1989 | Rosenstein et al. |
| 4,857,453 A | 8/1989 | Ullman et al. |
| 4,877,586 A | 10/1989 | Devaney, Jr. et al. |
| 4,877,747 A | 10/1989 | Stewart |
| 4,895,017 A | 1/1990 | Pyke et al. |
| 4,916,056 A | 4/1990 | Brown, III et al. |
| 4,917,503 A | 4/1990 | Bhattacharjee |
| 4,962,024 A | 10/1990 | Schulte |
| 5,023,053 A | 6/1991 | Finlan |
| 5,055,265 A | 10/1991 | Finlan |
| 5,063,081 A | 11/1991 | Cozzette et al. |
| 5,064,619 A | 11/1991 | Finlan |
| 5,075,077 A | 12/1991 | Durley, III et al. |
| 5,114,676 A | 5/1992 | Leiner et al. |
| 5,120,662 A | 6/1992 | Chan et al. |
| 5,124,254 A | 6/1992 | Hewlins et al. |
| 5,137,609 A | 8/1992 | Manian et al. |
| 5,143,854 A | 9/1992 | Pirrung et al. |
| 5,145,784 A | 9/1992 | Cox et al. |

(Continued)

FOREIGN PATENT DOCUMENTS

EP          0073593 A1      3/1983

(Continued)

OTHER PUBLICATIONS

Abstract of Article entitled *One-step all-in-one dry reagent immunoassays with fluorescent europium chelate label and time-resolved fluorometry*, T. Lovgren, L, Merio, K. Mitrunen, M. L. Makinen, M. Makela, K. Blomberg, T. Palenius, and K. Pettersson, Clinical Chemistry, vol. 42, 1996, pp. 1196-1201.
Abstract of DE10024145A1, Nov. 22, 2001.
Abstract of Japanese Patent No. JP 8062214, Mar. 8, 1996.
Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.

(Continued)

*Primary Examiner* — Jon P Weber
*Assistant Examiner* — Bin Shen
(74) *Attorney, Agent, or Firm* — Dority & Manning, P.A.

(57) ABSTRACT

A technique for detecting the presence or quantity of an enzyme (or enzyme inhibitor) and/or an amine within a test sample is provided. For example, in one embodiment, a diagnostic test kit is employed that utilizes reactive complexes that each includes a substrate joined (e.g., covalently bonded, physically adsorbed, etc.) to a reporter and a separation species. Upon contacting the reactive complexes, enzymes may cleave the substrate and release the reporter. Moreover, the test kit may also employ a chemichromic dye, i.e., a dye that exhibits a detectable color change upon chemical reaction with one or more functional groups, such as amino groups. The signal generated (directly or indirectly) by the reporter and chemichromic dye may then be used to indicate the presence or quantity of an enzyme (or enzyme inhibitor) and amine, respectively, within the test sample.

7 Claims, 3 Drawing Sheets

U.S. PATENT DOCUMENTS

| | | |
|---|---|---|
| 5,156,953 A | 10/1992 | Litman et al. |
| 5,179,288 A | 1/1993 | Miffitt et al. |
| 5,221,454 A | 6/1993 | Manian et al. |
| 5,234,813 A | 8/1993 | McGeehan et al. |
| 5,238,815 A | 8/1993 | Higo et al. |
| 5,242,828 A | 9/1993 | Bergström et al. |
| 5,252,459 A | 10/1993 | Tarcha et al. |
| 5,262,299 A | 11/1993 | Evangelista et al. |
| 5,268,306 A | 12/1993 | Berger et al. |
| 5,292,652 A | 3/1994 | Dovey et al. |
| 5,328,831 A | 7/1994 | Stewart et al. |
| 5,330,898 A | 7/1994 | Bar-Or et al. |
| 5,342,759 A | 8/1994 | Litman et al. |
| 5,356,782 A | 10/1994 | Moorman et al. |
| 5,358,852 A | 10/1994 | Wu |
| 5,376,255 A | 12/1994 | Gumbrecht et al. |
| 5,387,503 A | 2/1995 | Selmer et al. |
| 5,395,754 A | 3/1995 | Lambotte et al. |
| 5,424,219 A | 6/1995 | Jirikowski |
| 5,432,057 A | 7/1995 | Litman et al. |
| 5,436,161 A | 7/1995 | Bergström et al. |
| 5,451,683 A | 9/1995 | Barrett et al. |
| 5,464,739 A | 11/1995 | Johnson et al. |
| 5,467,778 A | 11/1995 | Catt et al. |
| 5,482,867 A | 1/1996 | Barrett et al. |
| 5,489,678 A | 2/1996 | Fodor et al. |
| 5,500,350 A | 3/1996 | Baker et al. |
| 5,504,013 A | 4/1996 | Senior |
| 5,508,171 A | 4/1996 | Walling et al. |
| 5,514,559 A | 5/1996 | Markert-Hahn et al. |
| 5,516,635 A | 5/1996 | Ekins et al. |
| 5,518,883 A | 5/1996 | Soini |
| 5,527,711 A | 6/1996 | Tom-Moy et al. |
| 5,554,539 A | 9/1996 | Chadney et al. |
| 5,554,541 A | 9/1996 | Malmqvist et al. |
| 5,569,608 A | 10/1996 | Sommer |
| 5,571,684 A | 11/1996 | Lawrence et al. |
| 5,585,273 A | 12/1996 | Lawrence et al. |
| 5,585,279 A | 12/1996 | Davidson |
| 5,589,401 A | 12/1996 | Hansen et al. |
| 5,658,443 A | 8/1997 | Yamamoto et al. |
| 5,670,381 A | 9/1997 | Jou et al. |
| 5,700,636 A | 12/1997 | Sheiness et al. |
| 5,726,064 A | 3/1998 | Robinson et al. |
| 5,753,517 A | 5/1998 | Brooks et al. |
| 5,780,308 A | 7/1998 | Ching et al. |
| 5,786,137 A | 7/1998 | Diamond et al. |
| 5,798,273 A | 8/1998 | Shuler et al. |
| 5,811,526 A | 9/1998 | Davidson |
| 5,827,748 A | 10/1998 | Golden |
| 5,834,226 A | 11/1998 | Maupin |
| 5,837,429 A | 11/1998 | Nohr et al. |
| 5,872,261 A | 2/1999 | Bremmer et al. |
| 5,876,944 A | 3/1999 | Kuo |
| 5,885,527 A | 3/1999 | Buechler |
| 5,906,921 A | 5/1999 | Ikeda et al. |
| 5,910,286 A | 6/1999 | Lipskier |
| 5,910,447 A | 6/1999 | Lawrence et al. |
| 5,922,537 A | 7/1999 | Ewart et al. |
| 5,932,410 A | 8/1999 | Whittaker et al. |
| 5,951,492 A | 9/1999 | Douglas et al. |
| 5,981,207 A | 11/1999 | Burbaum et al. |
| 6,030,792 A | 2/2000 | Otterness et al. |
| 6,080,391 A | 6/2000 | Tsuchiya et al. |
| 6,099,484 A | 8/2000 | Douglas et al. |
| 6,103,537 A | 8/2000 | Ullman et al. |
| 6,117,090 A | 9/2000 | Caillouette |
| 6,136,549 A | 10/2000 | Feistel |
| 6,136,611 A | 10/2000 | Saaski et al. |
| 6,151,110 A | 11/2000 | Markart |
| 6,165,798 A | 12/2000 | Brooks |
| 6,171,870 B1 | 1/2001 | Freitag |
| 6,177,281 B1 | 1/2001 | Manita |
| 6,183,972 B1 | 2/2001 | Kuo et al. |
| 6,184,042 B1 | 2/2001 | Neumann et al. |
| 6,194,220 B1 | 2/2001 | Malick et al. |
| 6,197,537 B1 | 3/2001 | Rao et al. |
| 6,200,820 B1 | 3/2001 | Hansen et al. |
| 6,221,238 B1 | 4/2001 | Grundig et al. |
| 6,234,974 B1 | 5/2001 | Catt et al. |
| 6,235,241 B1 | 5/2001 | Catt et al. |
| 6,235,464 B1 | 5/2001 | Henderson et al. |
| 6,235,471 B1 | 5/2001 | Knapp et al. |
| 6,241,863 B1 | 6/2001 | Monbouquette |
| 6,242,268 B1 | 6/2001 | Wieder et al. |
| 6,243,980 B1 | 6/2001 | Bronstein et al. |
| 6,251,621 B1 | 6/2001 | Lawrence et al. |
| 6,255,066 B1 | 7/2001 | Louderback |
| 6,284,472 B1 | 9/2001 | Wei et al. |
| 6,287,871 B1 | 9/2001 | Herron et al. |
| 6,294,392 B1 | 9/2001 | Kuhr et al. |
| 6,348,186 B1 | 2/2002 | Sutton et al. |
| 6,348,319 B1 | 2/2002 | Braach-Maksvytis et al. |
| 6,368,875 B1 | 4/2002 | Geisberg |
| 6,399,295 B1 | 6/2002 | Kaylor et al. |
| 6,436,722 B1 | 8/2002 | Clark et al. |
| 6,448,091 B1 | 9/2002 | Massey et al. |
| 6,451,607 B1 | 9/2002 | Lawrence et al. |
| 6,451,619 B1 | 9/2002 | Catt et al. |
| 6,455,861 B1 | 9/2002 | Hoyt |
| 6,461,496 B1 | 10/2002 | Feldman et al. |
| 6,485,926 B2 | 11/2002 | Nemori et al. |
| 6,509,196 B1 | 1/2003 | Brooks et al. |
| 6,511,814 B1 | 1/2003 | Carpenter |
| 6,528,321 B1 | 3/2003 | Fitzgerald et al. |
| 6,556,299 B1 | 4/2003 | Rushbrooke et al. |
| 6,562,631 B2 | 5/2003 | Braach-Maksvytis et al. |
| 6,566,508 B2 | 5/2003 | Bentsen et al. |
| 6,573,040 B2 | 6/2003 | Everhart et al. |
| 6,579,673 B2 | 6/2003 | McGrath et al. |
| 6,607,922 B2 | 8/2003 | LaBorde |
| 6,682,903 B2 | 1/2004 | Saunders |
| 6,720,007 B2 | 4/2004 | Walt et al. |
| 7,094,528 B2 | 8/2006 | Song et al. |
| 2001/0046668 A1 | 11/2001 | Levine et al. |
| 2002/0025541 A1 | 2/2002 | Nelson et al. |
| 2002/0146754 A1 | 10/2002 | Kitawaki et al. |
| 2002/0164659 A1 | 11/2002 | Rao et al. |
| 2003/0017615 A1 | 1/2003 | Sidwell et al. |
| 2003/0119073 A1 | 6/2003 | Quirk et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2003/0162236 A1 | 8/2003 | Harris et al. |
| 2004/0029205 A1 | 2/2004 | Small, Jr. et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0043512 A1 | 3/2004 | Song et al. |
| 2004/0096918 A1 | 5/2004 | Martin et al. |
| 2004/0106190 A1 | 6/2004 | Yang et al. |
| 2004/0121480 A1 | 6/2004 | Wei et al. |
| 2005/0112780 A1 | 5/2005 | Song |
| 2005/0191704 A1 | 9/2005 | Boga et al. |
| 2006/0003394 A1 | 1/2006 | Song |

FOREIGN PATENT DOCUMENTS

| | | |
|---|---|---|
| EP | 0244932 A2 | 11/1987 |
| EP | 0244932 A3 | 11/1987 |
| EP | 0420053 A1 | 4/1991 |
| EP | 0437287 B1 | 7/1991 |
| EP | 0617285 A2 | 9/1994 |
| EP | 0617285 A3 | 9/1994 |
| EP | 0703454 A1 | 3/1996 |
| EP | 0462376 B1 | 7/1996 |
| EP | 0724156 A1 | 7/1996 |
| EP | 0859230 A1 | 8/1998 |
| EP | 0898169 B1 | 2/1999 |
| EP | 1221616 A1 | 7/2002 |
| EP | 1422525 A1 | 5/2004 |
| WO | WO 9105999 A2 | 5/1991 |
| WO | WO 9221769 A1 | 12/1992 |
| WO | WO 9221770 A1 | 12/1992 |
| WO | WO 9221975 A1 | 12/1992 |
| WO | WO 9413835 A1 | 6/1994 |
| WO | WO 9415193 A1 | 7/1994 |
| WO | WO 9709620 A1 | 3/1997 |

| WO | WO 9910742 A1 | 3/1999 |
| WO | WO 9930131 A1 | 6/1999 |
| WO | WO 9936777 A1 | 7/1999 |
| WO | WO 9964864 A1 | 12/1999 |
| WO | WO 0019199 A1 | 4/2000 |
| WO | WO 0023805 A1 | 4/2000 |
| WO | WO 0047983 A1 | 8/2000 |
| WO | WO 0050891 A1 | 8/2000 |
| WO | WO 0078917 A1 | 12/2000 |
| WO | WO 0138873 A2 | 5/2001 |
| WO | WO 0163299 A1 | 8/2001 |
| WO | WO 0198765 A1 | 12/2001 |
| WO | WO 0198785 A2 | 12/2001 |
| WO | WO 03023051 A2 | 3/2003 |
| WO | WO 03023051 A3 | 3/2003 |
| WO | WO 03085403 A1 | 10/2003 |
| WO | WO 2005066359 A1 | 7/2005 |
| WO | WO 2006079826 A1 | 8/2006 |
| WO | WO 2007096637 A1 | 8/2007 |
| WO | WO 2007128980 A1 | 11/2007 |

OTHER PUBLICATIONS

Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.

Article—*Attempts to Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.

Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.

Article—*Detection of Protease Activity with a Fluorescence-labelled Peptide Substrate on a TLC Plate*, Uchikoba et al., Biosci. Biotechnol. Biochem., 64 (6), 2000, pp. 1285-1287.

Article—*Coloimetric and Fluorimetric Microplate Assays for Legumain and a Staining Reaction for Detection of the Enzyme after Electrophoresis*. Johansen et al., Analytical Biochemistry, 273, 1999, pp. 278-283.

Article—*Effect of matrix metalloprotease inhibitors on the 95 kDa metallopeptidase of Candida albicans*, C. Imbert, C. Kauffmann-Lacroix, G. Daniault, J. L. Jacquemin, and M. H. Rodier, Journal of Antimicrobial Chemotherapy, vol. 99, 2002, pp. 1007-1010.

Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S, Dulcey, Paul E. Schoen, and Frances S. Ligler, Analytical Biochemistry, vol. 208, 1993, pp. 197-205.

Article—*Flow-Based Microimmunoassay*, Analytical Chemistry, vol. 73, No. 24, Mark A. Hayes, Nolan A. Polson, Allison, N. Phayre, and Antonia A. Garcia, Dec. 15, 2001, pp. 5896-5902.

Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*Latex Immunoassays*, Leigh B. Bangs, Journal of Clinical Immunoassay, vol. 13, No. 3, 1990, pp. 127-131.

Article—*One step all-in one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palemius, and Kim Pettersson, Clinical Chemistry 42:8, 1996, pp. 1196-1201.

Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.

Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

Search Report and Written Opinion for PCT/US2005/011050, Sep. 19, 2005.

US 7,964,340 B2

ONE-STEP ENZYMATIC AND AMINE DETECTION TECHNIQUE

RELATED APPLICATIONS

The present application is a divisional of U.S. application Ser. No. 10/881,010, filed on Jun. 30, 2004, which is incorporated herein in its entirety by reference thereto.

BACKGROUND OF THE INVENTION

The rapid diagnosis of infection is becoming increasingly important to improving the effectiveness of subsequent treatment. Vaginal infection ("vaginitis"), for example, exists in three primary forms, i.e., bacterial vaginosis, candidal vaginitis ("yeast"), and trichomonas vaginitis ("trich"). Various techniques have been developed in an attempt to rapidly diagnose individual forms of vaginitis. Bacterial vaginosis, for example, has been diagnosed using "clue cells" (vaginal epithelial cells with adherent surface bacteria). However, conventional techniques for confirming the presence of "clue cells" are often complicated and slow. Techniques have been utilized that detect an elevated pH level in an infected sample.

Bacterial vaginosis and trichomonas vaginitis (primarily caused by the protozoan, *Trichomonas vaginalis*) may also cause a "fishy" odor that stems from an elevated level of amines, such as putrescine (1,4-diaminobutane), cadaverine (1,5-diamino pentane), trimethylamine, etc., in an infected vaginal sample. In bacterial vaginosis, for instance, amines are believed to be produced by members of anaerobic bacteria, prevotella, bacteroides, mobiluncus, and peptococcus. One conventional test for detecting the presence of amines in a vaginal test sample is known as the "Whiff test", which involves adding a strong alkali to a sample to form an enhanced odor. Unfortunately, such tests are undesired in that they require performance by a professional and utilize caustic chemicals. Another conventional technique for detecting amines in a sample is described in U.S. Pat. No. 5,124,254 to Hewlins, et al. Hewlins, et al. uses a diamine oxidase that reacts with diamines, such as putrescine and cadaverine, to give hydrogen peroxide. The hydroxen peroxide is then detected by a chromogenic system.

Various attempts at diagnosing candidal vaginitis, which is primarily caused by the presence of the yeast, *Candida albicans*, have also been developed. One such method involves detecting the presence of enzymes thought to act as a virulence factor for *Candida albicans*, such as proteases (e.g., aspartic protease) and/or peptidases (e.g., metallopeptidases). For example, U.S. Pat. No. 5,585,273 to Lawrence, et al. describes an enzyme assay for detecting *Candida albicans* aspartic protease. In Lawrence, et al., a sample, e.g., vaginal fluid, is contacted with a solid support having a reporter enzyme immobilized thereon. The reporter enzyme is releasable from the solid support upon action of an enzymatically active aspartic protease. After contacting the solid support, the sample is combined with an indicator susceptible to a visible or detectable change upon action of the reporter enzyme. If the indicator undergoes a detectable change, enzymatically active aspartic protease is present.

Unfortunately, the techniques described above suffer from significant disadvantages. One significant disadvantage is that many conventional techniques are unable to detect multiple forms of infection in a single test sample. In addition, many conventional techniques are too slow, costly, and complex for ordinary consumer use. As such, a need currently exists for a technique for detecting multiple forms of infection in a single test sample, which is fast, inexpensive, and easy to use.

SUMMARY OF THE INVENTION

In accordance with one embodiment of the present invention, a diagnostic test kit for detecting an amine, enzyme, or enzyme inhibitor within a test sample (e.g., vaginal fluid) is disclosed. The kit comprises a plurality of reactive complexes that each comprises a substrate joined to a reporter and a separation species. The substrate is cleavable by an enzyme to release the reporter. The kit further comprises a chromatographic medium that defines a first enzyme detection zone within which an enzyme detection signal is capable of being generated. The presence or quantity of an enzyme, or an inhibitor thereof, is determinable from the enzyme detection signal. The chromatographic medium further defines an amine detection zone within which is contained a chemichromic dye. The chemichromic dye is capable of undergoing a color change in the presence of an amine, wherein the presence or quantity of an amine is determinable from the color change.

In accordance with another embodiment of the present invention, a method for detecting an amine, enzyme, or enzyme inhibitor within a test sample is disclosed. The method comprises: i) contacting the test sample with a chromatographic medium, the chromatographic medium defining an enzyme detection zone and an amine detection zone, wherein an enzyme detection signal is capable of being generated within the enzyme detection zone and an amine detection signal is capable of being generated within the amine detection zone; ii) determining the presence or quantity of an enzyme or enzyme inhibitor from the enzyme detection signal; and iii) determining the presence or quantity of an amine from the amine detection signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
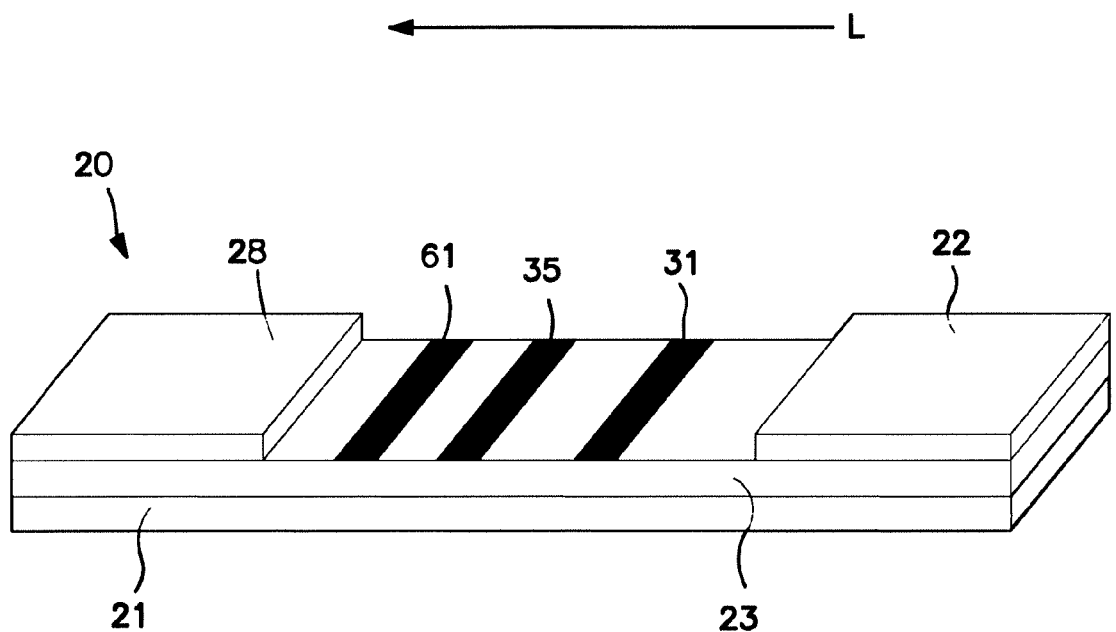
FIG. 1 is a perspective view of one embodiment of an assay device that may be used in the diagnostic test kit of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "test sample" generally refers to a material suspected of containing an enzyme, enzyme inhibitor, and/or amine of interest. For example, the test sample may be obtained or derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth. Besides physiological fluids, other liquid samples may be used such as water, food products, and so forth, for the performance of environmental or food production assays. In addition, a solid material may be used as the test sample. The test sample may be used directly as obtained from a source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium, to release the enzyme, enzyme inhibitor, amine, etc.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a technique for detecting the presence or quantity of an enzyme (or enzyme inhibitor) and/or an amine within a test sample. For example, in one embodiment, a diagnostic test kit is employed that utilizes reactive complexes that each includes a substrate joined (e.g., covalently bonded, physically adsorbed, etc.) to a reporter and a separation species. Upon contacting the reactive complexes, enzymes may cleave the substrate and release the reporter. Moreover, the test kit may also employ a chemichromic dye, i.e., a dye that exhibits a detectable color change upon chemical reaction with one or more functional groups, such as amino groups. The signal generated (directly or indirectly) by the reporter and chemichromic dye may then be used to indicate the presence or quantity of an enzyme (or enzyme inhibitor) and amine, respectively, within the test sample.

I. Enzyme or Enzyme Inhibitor Detection

Various types of enzymes may be detected in accordance with the present invention. For instance, transferases, hydrolases, lyases, and so forth, may be detected. In some embodiments, the enzyme of interest is a "hydrolase" or "hydrolytic enzyme", which refers to enzymes that catalyze hydrolytic reactions. Examples of such hydrolytic enzymes include, but are not limited to, proteases, peptidases, lipases, nucleases, homo- or hetero-oligosaccharidases, homo- or hetero-polysaccharidases, phosphatases, sulfatases, neuraminidases and esterases. In one embodiment, for example, peptidases may be detected. "Peptidases" are hydrolytic enzymes that cleave peptide bonds found in shorter peptides. Examples of peptidases include, but are not limited to, metallopeptidases; dipeptidylpeptidase I, II, or IV; and so forth. In another embodiment, proteases may be detected. "Proteases" are hydrolytic enzymes that cleave peptide bonds found in longer peptides and proteins. Examples of proteases that may be detected according to the present invention include, but are not limited to, serine proteases (e.g., chymotrypsin, trypsin, elastase, PSA, etc.), aspartic proteases (e.g., pepsin), thiol proteases (e.g., prohormone thiol proteases), metalloproteases, acid proteases, and alkaline proteases. Still other enzymes are described in U.S. Pat. No. 6,243,980 to Bronstein, et al. and 2004/0081971 to Yue, et al., which are incorporated herein in their entirety by reference thereto for all purposes.

Likewise, any of a variety of known enzyme inhibitors may also be detected in accordance with the present invention. For example, known inhibitors of hydrolytic enzymes include, but are not limited to, inhibitors of proteases, peptidases, lipases, nucleases, homo- or hetero-oligosaccharidases, homo- or hetero-polysaccharidases, phosphatases, sulfatases, neuraminidases and esterases. Protease inhibitors may include, for instance, aspartic protease inhibitors, serine protease inhibitors, thiol protease inhibitors, metalloprotease inhibitors, acid or alkaline protease inhibitors, and so forth. Some specific examples of protease inhibitors include benzamideine, indole, pepstatin, ovomacroglobulin, haloperidol, transition state mimetics, and so forth.

Various techniques may generally be employed to detect the presence or quantity of an enzyme or enzyme inhibitor. For example, in some embodiments, reactive complexes are employed that each includes a substrate joined to a reporter and a separation species. The term "substrate" generally refers to a substance that is chemically acted upon by an enzyme to form a product. The substrate may occur naturally or be synthetic. Some suitable substrates for hydrolytic enzymes include, for instance, esters, amides, peptides, ethers, or other chemical compounds having an enzymatically-hydrolyzable bond. The enzyme-catalyzed hydrolysis reaction may, for example, result in a hydroxyl or amine compound as one product, and a free phosphate, acetate, etc., as a second product. Specific types of substrates may include, for instance, proteins or glycoproteins, peptides, nucleic acids (e.g., DNA and RNA), carbohydrates, lipids, esters, derivatives thereof, and so forth. For instance, some suitable substrates for peptidases and/or proteases may include peptides, proteins, and/or glycoproteins, such as casein (e.g., β-casein, azocasein, etc.), albumin (e.g., bovine serum albumin (BSA)), hemoglobin, myoglobin, keratin, gelatin, insulin, proteoglycan, fibronectin, laminin, collagen, elastin, and so forth. Still other suitable substrates are described in U.S. Pat. No. 4,748,116 to Simonsson, et al.; U.S. Pat. No. 5,786,137 to Diamond, et al.; U.S. Pat. No. 6,197,537 to Rao, et al.; and U.S. Pat. No. 6,235,464 to Henderson, et al.; U.S. Pat. No. 6,485,926 to Nemori, et al., which are incorporated herein in their entirety by reference thereto for all purposes.

The reporters may contain any substance capable of directly or indirectly generating a detectable signal. Suitable detectable substances may include, for instance, chromogens; luminescent compounds (e.g., fluorescent, phosphorescent, etc.); radioactive compounds; visual compounds (e.g., latex or metallic particles, such as gold); liposomes or other vesicles containing signal-producing substances; enzymes and/or substrates, and so forth. For instance, some enzymes suitable for use as detectable substances are described in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable reporters may be described in U.S. Pat. Nos. 5,670,381 to Jou, et al. and 5,252,459 to Tarcha, et al., which are incorporated herein in their entirety by reference thereto for all purposes.

In some embodiments, the reporters may contain a luminescent compound that produces an optically detectable signal. The luminescent compound may be a molecule, polymer, dendrimer, particle, and so forth. For example, suitable fluorescent molecules may include, but not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. Nos. 4,614,723 to Schmidt, et al.; 5,464,741 to Hendrix; 5,518,883 to Soini; 5,922,537 to Ewart, et al.; 6,004,530 to Sagner, et al.; and 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine] 2-[3-(4-methyl-2,2'-bipyridine-4-yl)propyl]-1,3-dioxolane ruthenium (II); bis(2,2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2, 2'bipyridine)ruthenium (II); (2,2'-bipyridine) [bis-bis(1,2-diphenylphosphino)ethylene] 2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. Nos. 6,613,583 to Richter, et al.; 6,468,741 to Massey, et al.; 6,444,423 to Meade, et al.; 6,362,011 to Massey, et al.; 5,731,147 to Bard, et al.; and 5,591,581 to Massey, et al., which are incorporated herein in their entirety by reference thereto for all purposes.

In some cases, "time-resolved" luminescent detection techniques are utilized. Time-resolved detection involves exciting a luminescent compound with one or more short pulses of light, then typically waiting a certain time (e.g., between approximately 1 to 100 microseconds) after excitation before measuring the remaining the luminescent signal. In this manner, any short-lived phosphorescent or fluorescent background signals and scattered excitation radiation are eliminated. This ability to eliminate much of the background signals may result in sensitivities that are 2 to 4 orders greater than conventional fluorescence or phosphorescence. Thus, time-resolved detection is designed to reduce background signals from the emission source or from scattering processes (resulting from scattering of the excitation radiation) by taking advantage of the characteristics of certain luminescent materials.

To function effectively, time-resolved techniques generally require a relatively long emission lifetime for the luminescent compound. This is desired so that the compound emits its signal well after any short-lived background signals dissipate. Furthermore, a long luminescence lifetime makes it possible to use low-cost circuitry for time-gated measurements. For example, the detectable compounds may have a luminescence lifetime of greater than about 1 microsecond, in some embodiments greater than about 10 microseconds, in some embodiments greater than about 50 microseconds, and in some embodiments, from about 100 microseconds to about 1000 microseconds. In addition, the compound may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, one suitable type of fluorescent compound for use in time-resolved detection techniques includes lanthanide chelates of samarium (Sm (III)), dysprosium (Dy (III)), europium (Eu (III)), and terbium (Tb (III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have exceptionally large Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent compound. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent compounds described above, other compounds that are suitable for use in the present invention may be described in U.S. Pat. Nos. 6,030,840 to Mullinax, et al.; 5,585,279 to Davidson; 5,573,909 to Singer, et al.; 6,242,268 to Wieder, et al.; and 5,637,509 to Hemmila, et al., which are incorporated herein in their entirety by reference thereto for all purposes.

As stated, the reporter may indirectly generate a detectable signal in some embodiments of the present invention. In such instances, the reporter may not specifically contain a detectable substance, but instead be capable of interacting with a detectable substance to generate a detection signal. For example, in some embodiments, the reporter may be a member of a specific binding pair, i.e., two different molecules where one of the molecules chemically and/or physically binds to the second molecule. Immunoreactive specific binding members may include antigens, haptens, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding members include, but are not limited to, biotin and avidin, streptavidin, neutravidin, captavidin, or an anti-biotin antibody; protein A and G; carbohydrates and lectins, complementary nucleotide sequences (including probe and capture nucleic acid sequences used in DNA hybridization assays to detect a target nucleic acid sequence); complementary peptide sequences including those formed by recombinant methods; effector and receptor molecules; hormone and hormone binding protein; enzyme cofactors and enzymes, enzyme inhibitors and enzymes; derivatives thereof, and so forth. Furthermore, specific binding pairs may include members that are analogs, derivatives, and/or fragments of the original specific binding member. When used to indirectly generate a signal, a reporter that is a member of a specific binding pair may be placed into contact with a probe conjugated with another member of the specific binding pair. Thus, the released reporter will bind to the conjugated probe, which may then be readily detected (directly or indirectly) using techniques well known to those skilled in the art.

Whether or not the reporter directly or indirectly generates a signal, it may contain particles (sometimes referred to as "beads" or "microbeads"). Among other things, particles enhance the ability of the reporter to travel through a chromatographic medium and become immobilized within a detection zone, such as described below. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex particles are labeled with a fluorescent or colored dye. Although any latex particle may be used, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. Nos. 5,670,381 to Jou, et al. and 5,252,459 to Tarcha, et al. Commercially available examples of suitable fluorescent particles include fluorescent carboxylated microspheres sold by Molecular Probes, Inc. under the trade names "FluoSphere" (Red 580/605) and "Transfluo-Sphere" (543/620), as well as "Texas Red" and 5- and 6-carboxytetramethylrhodamine, which are also sold by Molecular Probes, Inc. of Eugene, Oreg. In addition, commercially available examples of suitable colored, latex microparticles include carboxylated latex beads sold by Bangs Laboratories, Inc. of Fishers, Ind.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

In addition to being joined to a reporter, such as described above, the substrate is also joined to a separation species. The separation species may generally be any material that facilitates separation of released reporters from unreacted complexes. In some embodiments, for example, such separation is achieved through chemical binding. Specifically, the separation species may be a specific binding member, such as described above, which may bind to another member of the binding pair to accomplish the desired separation. When the reporter contains a specific binding member, it is generally desired that it is different than and has no specific binding affinity for the specific binding member of the separation species.

Besides chemical binding, other separation techniques may also be utilized. For instance, in one embodiment, magnetic separation techniques are employed. In such embodiments, the separation species may contain a magnetic substance. Generally, a material is considered "magnetic" or "magnetically responsive" if it is influenced by the application of a magnetic field, such as, for example, if it is attracted or repulsed or has a detectable magnetic susceptibility or induction. For instance, some examples of suitable magnetically responsive substances that may be used to impart magnetic properties include, but are not limited to, paramagnetic materials, superparamagnetic materials, ferromagnetic materials, ferrimagnetic materials, and metamagnetic materials. Specific examples are metals such as iron, nickel, cobalt, chromium, and manganese; lanthanide elements, such as neodymium, erbium; alloys, such as magnetic alloys of aluminum, nickel, cobalt, or copper; oxides, such as ferric oxide ($Fe_3O_4$), ferrous oxide ($Fe_2O_3$), chromium oxide ($CrO_2$), cobalt oxide (CoO), nickel oxide ($NiO_2$), or manganese oxide ($Mn_2O_3$); composite materials, such as ferrites; and solid solutions, such as magnetite with ferric oxide. In some embodiments of the present invention, the magnetic substance contains a magnetic particle. When utilized, the shape and/or size of the particles may vary, such as described above.

The separation species and reporter may generally be attached to the substrate using any of a variety of well-known techniques. For instance, covalent attachment of a separation species and/or reporter to a substrate may be accomplished using carboxylic, amino, aldehyde, bromoacetyl, iodoacetyl, thiol, epoxy and other reactive functional groups, as well as residual free radicals and radical cations, through which a coupling reaction may be accomplished. A surface functional group may also be incorporated as a functionalized co-monomer because the surface of the reporter may contain a relatively high surface concentration of polar groups. In certain cases, the separation species and/or reporter may be capable of direct covalent bonding to a substrate without the need for further modification. It should also be understood that, besides covalent bonding, other attachment techniques, such as physical adsorption, may also be utilized in the present invention. Still other non-covalent linkage techniques may employ antibodies and/or antigens, such as secondary antibodies (e.g., avidin, streptavidin, neutravidin, and/or biotin).

One particular technique for covalently bonding a reporter and separation species to a substrate will now be described in more detail. In this particular embodiment, the substrate is β-casein, the reporter is a dyed particle, and the separation species is a biotin derivative. For example, the reporter may be red carboxylated latex particles available from Molecular Probes, Inc. under the name "FluoSphere." Likewise, the separation species may be sulfosuccinimidyl-6-(biotinamido) hexanoate, which is available from Pierce Biotechnology, Inc. of Rockford, Ill. under the name EZ-Link® Sulfo-NHS-LC-Biotin. Techniques employed in making such NHS-activated biotins are believed to be described in U.S. Pat. No. 5,872,261 to Bremmer, et al., which is incorporated herein in its entirety by reference thereto for all purposes.

Figure 2:
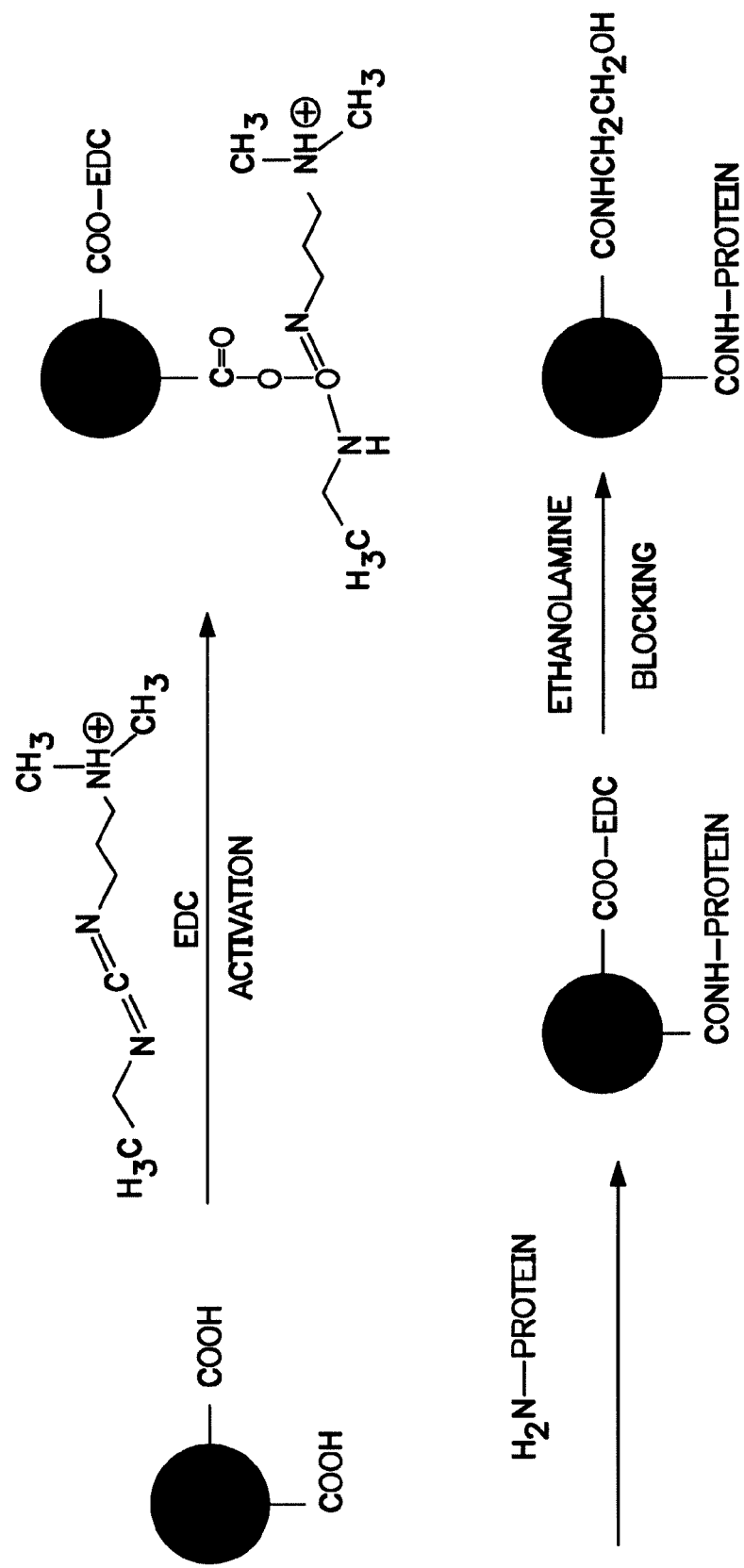
FIG. 2 is a graphical illustration of one embodiment for covalently bonding a reporter to a substrate.

To covalently conjugate the dyed particle with β-casein, the carboxylic groups on the particle surface are first activated with a carbodiimide (e.g., ethylcarbodiimide hydrochloride (EDC)), such as shown in FIG. 2. Because protein and glycoprotein substrates (e.g., β-casein) typically possess primary amine groups ($NH_2$), such as on the side chain of lysine (K) residues and/or the N-terminus of each polypeptide, the activated carboxylic acid groups may then be reacted with the primary amine (—$NH_2$) groups of the substrate to form an amide bond. This reaction may occur in a buffer, such as phosphate-buffered saline (PBS) (e.g., pH of 7.2), 2-(N-morpholino) ethane sulfonic acid (MES) (e.g., pH of 5.3), or borate buffer (e.g., pH of 8.5). If desired, the resulting reactive complexes may then be blocked with ethanolamine, for instance, to block any remaining activated sites.

In a somewhat similar manner, the biotin-based separation species may also be covalently bonded to β-casein. For example, NHS-activated biotins may form covalent amide bonds with the primary amine groups present on the substrate (optionally in the presence of a buffer). An example of such a reaction is set forth below:

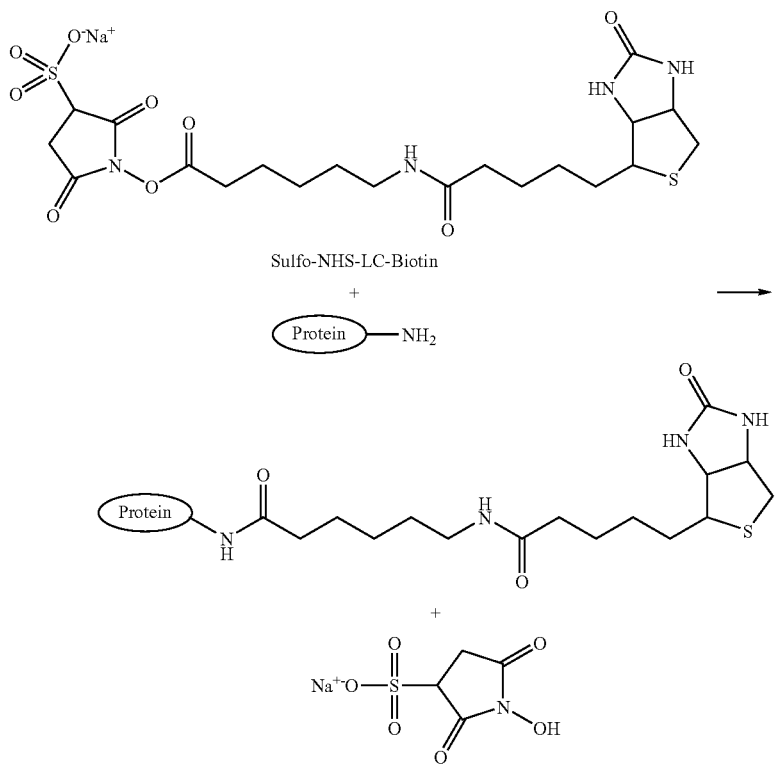

Once formed, a user may allow the test sample to incubate with the reactive complexes for a certain period of time. For example, those skilled in the art readily recognize that the time of incubation for an enzyme-catalyzed reaction depends on the activity of the enzyme of interest, which in turn depends on in part on the temperature, pH, substrate concentration, the presence of inhibitors (competitive (binds to enzyme), uncompetitive (binds to enzyme-substrate complex), or noncompetitive (binds to enzyme and/or enzyme-substrate complex)), and so forth. These factors may be selectively controlled as desired to increase or decrease the incubation time. For example, the time for incubation may be greater than about 1 minute, in some embodiments from about 5 to about 50 minutes, and in some embodiments, from about 10 to about 25 minutes. Likewise, the pH may be selectively controlled to facilitate enzyme activity. For example, high levels of basic substances (e.g., amines) within a test sample may result in a pH that is too high for optimum activity of some enzymes, e.g., greater than 8. Specifically, an enzyme may possess optimum activity at a pH level of from about 3 to about 8, and in some embodiments, from about 4 to about 7. Thus, if desired, a buffer or other pH-altering compound may be employed to maintain the desired pH.

After incubation, any enzyme present within the test sample will typically cleave the substrate of at least a portion of the reactive complexes. As a result, various materials may be formed, including released reporters, released separation species, partially cleaved complexes (e.g., enzyme-reporter-substrate-separation species), and unreacted complexes (e.g., reporter-substrate-separation species). Longer incubation times and greater enzyme concentrations may result in a greater concentration of released reporters and separation species in the resulting incubation mixture. Further, it should be understood that the "released" reporters and separation species may or may not contain fragments of the complex depending on the nature of the substrate and enzyme. For instance, when using longer chain substrates (e.g., proteins), the released reporters and separation species may contain peptide fragments from the protein substrate. On the other hand, when using shorter chain substrates (e.g., peptides), the released reporters and separation species may be relatively free of such fragments.

As stated above, various separation techniques may be utilized in the present invention for separating any released reporters from unreacted complexes including, but not limited to, chemical separation techniques, magnetic separation techniques, etc. In one particular embodiment, for example, the diagnostic test kit contains an assay device that employs a chromatographic medium for separating unreacted complexes from released reporters. In contrast to other techniques, such as centrifugation, the use of a chromatographic medium may simplify and reduce the costs of the resulting diagnostic test kit for many consumer applications, including those in which a disposable kit is desired. Further, the use of a chromatographic medium also provides for a mechanism in which two different species, i.e., an enzyme (or inhibitor) and amine, may be simultaneously tested in a single step. That is, a user may use the kit to test a single sample for an enzyme (or inhibitor) and/or amine.

Referring to FIG. 1, for instance, one embodiment of an assay device 20 that may be used in the present invention will now be described in more detail. As shown, the assay device 20 contains a chromatographic medium 23 optionally carried by a support 21. The chromatographic medium 23 may be made from any of a variety of materials through which a fluid is capable of passing, such as a fluidic channel, porous membrane, etc. For example, the chromatographic medium 23 may be a porous membrane formed from materials such as, but not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The support 21 may be formed from any material able to carry the chromatographic medium 23. Although not required, the support 21 may be transparent so that light readily passes therethrough. In addition, it is also generally desired that the support 21 is liquid-impermeable so that fluid flowing through the medium does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate structures are described in U.S. Pat. No. 5,075,077 to Durley, III, et al., which is incorporated herein in its entirety by reference thereto for all purposes.

The assay device 20 may also contain an absorbent material 28. The absorbent material 28 generally receives fluid that has migrated through the entire chromatographic medium 23. As is well known in the art, the absorbent material 28 may assist in promoting capillary action and fluid flow through the medium 23. The assay device 20 may also include a sample pad 22 or other material that is in fluid communication with the chromatographic medium 23. Some suitable materials that may be used to form the sample pad 22 include, but are not limited to, nitrocellulose, cellulose, porous polyethylene pads, and glass fiber filter paper. If desired, the sample pad 22 may contain one or more assay pretreatment reagents, either diffusively or non-diffusively attached thereto.

Generally speaking, the manner in which the assay device 20 functions may depend on the type of separation species selected for the reactive complexes. In this regard, various techniques for using the assay device 20 in embodiments in which the separation species is a specific binding member will now be described in more detail. For example, as stated above, the reactive complexes are generally allowed to incubate with the test sample for a certain period of time. This incubation process may be conducted before applying the test sample to the chromatographic medium 23, or it may be incorporated as part of the assaying procedure (i.e., incubation occurs after the test sample is applied, such as within an incubation well). For instance, the incubation mixture may be directly applied to a portion of the chromatographic medium 23 through which it may then travel in the direction illustrated by arrow "L" in FIG. 1. Alternatively, the mixture may first be applied to the sample pad 22.

Regardless, the chromatographic medium 23 defines a first enzyme detection zone 31 within which the separation species (e.g., specific binding member) may be captured and detected. For example, in one embodiment, a first receptive material is immobilized within the first enzyme detection zone 31 that serves as a stationary binding site for released specific binding members, specific binding members present on unreacted complexes, or specific binding members present on partially cleaved complexes. For example, in some embodiments, the first receptive material may be a biological receptive material. Such biological receptive materials are well known in the art and may include, but are not limited to, antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof. As the enzyme concentration begins to increase in the test sample, more reporters are released that have little or no specific binding affinity for the receptive material at the first enzyme detection zone 31. The reduced quantity of reporters at the first enzyme detection zone 31 thus results in a decrease in signal intensity. From this decrease in signal intensity, the presence or concentration of the enzyme may be readily determined. For example, in one embodiment, the amount of enzyme is inversely proportional to the signal intensity at the first enzyme detection zone 31, $I_1$. If desired, the signal intensity $I_1$ may be plotted versus the enzyme concentration for a range of known enzyme concentrations to generate an intensity curve. To determine the quantity of enzyme in an unknown test sample, the signal intensity may then be converted to enzyme concentration according to the intensity curve.

The first enzyme detection zone 31 may generally provide any number of distinct detection regions so that a user may better determine the concentration of an enzyme within a test sample. Each region may contain the same or different receptive materials. For example, the enzyme detection zone 31 may include two or more distinct detection regions (e.g., lines, dots, etc.). The use of two or more distinct detection regions may provide certain benefits, such as facilitating semi-quantitation and/or inhibiting potential false positives due to overrunning of the reactive complexes or other materials. The detection regions may be disposed in the form of lines in a direction substantially perpendicular to the flow of the test sample through the chromatographic medium 23. Likewise, in some embodiments, the detection regions may be disposed in the form of lines in a direction substantially parallel to the flow of the test sample through the medium 23. It should be understood that one or more distinct regions of the first enzyme detection zone 31 may exhibit the above-described relationship between signal intensity and enzyme concentration; however, each distinct region need not exhibit such a relationship. For example, in some embodiments, only one of multiple distinct regions may exhibit a signal intensity that is inversely proportional to the concentration of the enzyme. The signal intensity of other distinct regions, such as those used to reduce false positives, may otherwise remain constant, or exhibit an increase and/or decrease in signal intensity. So long as at least one distinct region of the enzyme detection zone 31 satisfies the inverse relationship, the signal intensity exhibited by the first enzyme detection zone 31 is considered inversely proportional to the enzyme concentration.

The level of detection sensitivity for the enzyme of interest may be selectively controlled depending on the desired application. One particular technique for controlling the detection sensitivity involves manipulating the quantity of the first receptive material used in the first enzyme detection zone 31. For instance, when assaying samples suspected of containing large concentrations of an enzyme, the quantity of the first receptive material may be equal to or greater than the minimum required to capture the total quantity of reactive complexes utilized. Thus, if no enzyme were present in the test sample, all of the reactive complexes would become immobilized at the enzyme detection zone 31 and all of the reporters would be present within the first enzyme detection zone 31. The minimum quantity required to capture all of the reactive complexes may be determined experimentally, and generally depends upon the amount of the reactive complexes used and the binding affinity between the first receptive material and the specific binding member.

In applications where enhanced detection sensitivity is desired (e.g., low suspected enzyme concentrations or short incubation times), the quantity of the first receptive material may be less than the minimum required to capture the total quantity of reactive complexes utilized. The use of such a limited quantity of the first receptive material may provide a variety of benefits, including decreasing the likelihood that any partially cleaved complexes are captured at the first enzyme detection zone 31, which would otherwise result in a measured enzyme concentration that is slightly lower than the actual concentration. That is, as the concentration of the enzyme increases, more specific binding members are released from the reactive complexes. Due to their smaller molecular size, these released specific binding members generally reach the first enzyme detection zone 31 faster than the partially cleaved complexes and unreacted complexes, and thus have a higher probability of occupying the available binding sites. Further, the partially cleaved complexes also generally contain a lesser quantity of specific binding members than those that are completely unreacted. This reduction in the quantity of specific binding members statistically decreases the chance that the partially cleaved complexes will bind to the first enzyme detection zone 31.

As discussed above, the inverse relationship between enzyme concentration and signal intensity may be correlated to the actual enzyme concentration in the test sample. However, because it is not always desirable to use an assay format that correlates an "increase" in enzyme concentration to a "decrease" in signal intensity (e.g. consumer applications), the present invention also provides for embodiments in which an "increase" in enzyme concentration is directly correlated to an "increase" in signal intensity. In such cases, additional enzyme detection zones may be utilized. For example, referring again to FIG. 1, the chromatographic medium 23 may also define a second enzyme detection zone 35 positioned downstream from the first enzyme detection zone 31. The second enzyme detection zone 35 may provide one or more distinct regions (e.g., line, dot, etc.), and may be positioned at any orientation relative to the flow of the test sample.

Within the second enzyme detection zone 35, any released reporters, partially cleaved complexes, or unreacted complexes that do not bind to the first receptive material at the enzyme detection zone 31 may be captured and detected. The manner in which the released reporters are captured may depend on the nature of the reporters utilized. In some embodiments, a second receptive material may be immobilized within the second enzyme detection zone 35 for capturing reporters. For example, the second receptive material may be a biological receptive material, such as, but not limited to, antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof. Because the second receptive material desirably binds specifically to the reporters, it is normally different than the first receptive material.

For example, the released reporter may be conjugated with a specific binding member selected to have an affinity for the second receptive material within the second enzyme detection zone 35. The specific binding member may be conjugated to the reporter using any of a variety of well-known techniques, such as through covalent bonding and/or physical adsorption in a manner such as described above. In one particular embodiment, carboxylic groups of the reporter are activated and reacted with amino groups of an antibody to form an amide bond. In this instance, the released reporter may become immobilized within the second enzyme detection zone 35 through specific binding between the antibody and a receptive material so that the signal generated by the detectable substance may be detected. For example, the first receptive material may be a secondary antibody (such as an anti-biotin antibody, e.g., goat anti-Mouse IgG antibody), avidin (a highly cationic 66,000-dalton glycoprotein), streptavidin (a nonglycosylated 52,800-dalton protein), neutravidin (a deglysolated avidin derivative), or captavidin (a nitrated avidin derivative). In this embodiment, the first receptive material may bind to a biotin (Mouse IgG antibody) specific binding member. The reporter may, for instance, be a fluorescent-dyed particle conjugated with C-reactive protein, which may bind to a monoclonal antibody second receptive material (e.g., anti C-reactive protein (CRP) monoclonal antibody).

Of course, any other suitable technique for capturing and detection the released reporters may also be used. For example, in some embodiments, non-biological receptive materials may be immobilized within the second enzyme detection zone 35 for capturing released reporters. Such non-biological receptive materials may be particularly useful in capturing, for example, released reporters that contain labeled particles. For instance, in one embodiment, the receptive material is a polyelectrolyte. Polyelectrolytes may have a net positive or negative charge, as well as a net charge that is generally neutral. Some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada. Further examples of polyelectrolytes are described in more detail in U.S. Patent App. Publication No. 2003/0124739 to Song, et al., which is incorporated herein in it entirety by reference thereto for all purposes.

Although any polyelectrolyte may generally be utilized, the polyelectrolyte selected for a particular application may vary depending on the nature of the released reporters. In particular, the distributed charge of a polyelectrolyte allows it to bind to substances having an opposite charge. Thus, for example, polyelectrolytes having a net positive charge are often better equipped to bind with released reporters (e.g., dyed particles) that are negatively charged, while polyelectrolytes that have a net negative charge are often better equipped to bind to released reporters that are positively charged. Thus, in such instances, the ionic interaction between these molecules allows the required binding to occur within the second enzyme detection zone 35. Nevertheless, although ionic interaction is primarily utilized to achieve the desired binding, it has also been discovered that polyelectrolytes may bind with reporters having a similar charge.

Besides using receptive materials, other capturing techniques may also be utilized. For example, in one embodiment, the reporter may contain a magnetic substance that is capable of being captured by a magnetic device. In one embodiment, the magnetic device is positioned adjacent to (e.g., below) the second enzyme detection zone 35 defined by the chromatographic medium 23. In this manner, the magnetic device may immobilize the released reporters, as well as any partially cleaved or unreacted complexes, within the second enzyme detection zone 35. Any magnetic device may be used in the present invention. A magnetic field generator, for instance, may be used to generate a magnetic field that elicits a response from the magnetic substances. Suitable magnetic field generators include, but are not limited to, permanent magnets and electromagnets. Some commercially available examples of suitable magnetic separation devices include the Dynal MPC series of separators manufactured by Dynal, Inc. of Lake Success, N.Y., which employ a permanent magnet located externally to a container holding a test medium. Still other magnetic devices may be described in U.S. Pat. Nos. 5,200,084 to Liberti, et al.; 5,647,994 to Tuunanen, et al.; 5,795,470 to Wang, et al.; and 6,033,574 to Siddigi, which are incorporated herein in their entirety by reference thereto for all purposes.

When the reporters contain a substance that is directly detectable, an increase in enzyme concentration results in an increase in the signal intensity at the second enzyme detection zone 35, $I_2$, due to the presence of released reporters and/or partially cleaved complexes. From this increase in signal intensity, the presence or concentration of the enzyme may be readily determined. For example, in one embodiment, the amount of enzyme is directly proportional to the signal intensity at the second enzyme detection zone 35, $I_2$. If desired, the signal intensity $I_2$ may be plotted versus the enzyme concentration for a range of known enzyme concentrations to generate an intensity curve. To determine the quantity of enzyme in an unknown test sample, the signal intensity may then be converted to enzyme concentration according to the intensity curve. It should be understood that, as discussed above with respect to the first enzyme detection zone 31, so long as one distinct region of the second enzyme detection zone 35 satisfies the direct relationship, the signal intensity exhibited by the second enzyme detection zone 35 is considered directly proportional to the enzyme concentration.

Also, an inverse relationship may exist between the signal intensity at the first enzyme detection zone 31 ($I_1$) and the second enzyme detection zone 35 ($I_2$). For example, because a predetermined amount of reporters are present, the amount captured at the second enzyme detection zone 35 is inversely proportional to the amount captured at the first enzyme detection zone 31. As a result of this inverse relationship, the concentration of the enzyme may, in some cases, be more effectively measured over an extended range by comparing the signal intensity at both detection zones. For example, in one embodiment, the amount of enzyme is directly proportional to the ratio of the signal intensity "$I_2$" to the signal intensity "$I_1$." Based upon the range in which this ratio falls, the general concentration range for the enzyme may be determined. If desired, the ratio of $I_2$ to $I_1$ may be plotted versus enzyme concentration for a range of known enzyme concentrations to generate an intensity curve. To determine the quantity of enzyme in an unknown test sample, the signal intensity ratio may then be converted to enzyme concentration according to the intensity curve. It should be noted that alternative mathematical relationships between $I_1$ and $I_2$ may be plotted versus the enzyme concentration to generate the intensity curve. For example, in one embodiment, the value of $I_2/(I_2+I_1)$ may be plotted versus enzyme concentration to generate the intensity curve.

As stated above, certain embodiments of the present invention may utilize a reporter that is not directly detectable. Thus, when released, it is generally desired that the reporter interact in some manner with a detectable substance for subsequent detection. For example, probes capable of generating a detectable signal may be employed that are configured to bind to the released reporters. For example, probes may contain particles labeled or otherwise applied with the detectable substance. In some instances, it is desired to modify the probes in some manner. For example, the probes may be modified with a specific binding member to form conjugated probes that have specific affinity for the released reporters. The specific binding members may generally be conjugated to the probes using any of a variety of well-known techniques, such as through covalent bonding and/or physical adsorption in a manner such as described above. In one particular embodiment, carboxylic groups on the probe surface are activated and reacted with amino groups of the specific binding member to form an amide bond. When utilized, it is generally desired that the specific binding pair used for the probes and reporter is different than the specific binding pair used for the first receptive material and the other specific binding member joined to the substrate. This helps to ensure that the probes and reporters do not substantially interfere with the binding mechanism described above.

The probes may be contacted with the released reporters at any stage of the enzyme detection process. For example, in some embodiments, the probes may be applied to the assay device 20 at a location upstream from the region in which detection is desired. For example, in one embodiment, the probes may be applied to a conjugated pad (not shown) that is located upstream from the enzyme detection zones 31 and 35, but downstream from the sample pad 22.

In this embodiment, a variety of assay formats may be used to detect the released reporters. In one embodiment, for example, a "sandwich" assay format is utilized in which the released reporter is selected to have an affinity for the specific binding member of the conjugated probe. The released reporter, such as antibodies, antigens, etc., typically has two or more binding sites (e.g., epitopes). One of these binding sites becomes occupied by the specific binding member of the conjugated probe. However, the free binding site of the released reporter may subsequently bind to a receptive material immobilized within the second enzyme detection zone 35 to form a new ternary sandwich complex. Alternatively, the released reporter may be detected using direct or indirect "competitive" assay formats. In such instances, the specific binding member of the conjugated probe may be the same as or an analog of the released reporter. Thus, upon reaching the second enzyme detection zone 35, the conjugated detection probes and the released reporters compete for available binding sites of the immobilized receptive material. Of course, any other assay format is also suitable for use in the present invention.

For the embodiments described above in which the reporters are indirectly detectable, an increase in enzyme concentration within the test sample results in the release in a greater number of reporters. Thus, if a sandwich assay format is used, more released reporters bind to the conjugated probes so that the amount of enzyme is directly proportional to the signal intensity at the second enzyme detection zone 35. On the other hand, if a competitive assay format is used, the amount of enzyme is inversely proportional to the signal intensity at the second enzyme detection zone 35. In any event, the signal intensity may be plotted versus the enzyme concentration for a range of known enzyme concentrations to generate an intensity curve. To determine the quantity of enzyme in an unknown test sample, the signal intensity may then be converted to enzyme concentration according to the intensity curve.

Besides techniques in which the separation species is chemically separated from the reporter, other separation techniques are also contemplated in the present invention. For example, in one embodiment of the present invention, the separation species contains a magnetic substance, such as described above. Thus, during and/or after incubation, any released magnetic substances, partially cleaved reactive complexes, and unreacted complexes may be removed from the incubation mixture using a magnetic field. Once the magnetic substances (including partially cleaved and unreacted complexes) are removed, the remaining portion of the incubation mixture (e.g., the supernatant) may be tested for the presence of an enzyme. Generally speaking, as enzyme concentration begins to increase in the test sample, more reporters become released that are free from a magnetic substance and are thus not removed during magnetic separation. Consequently, enzyme concentration correlates to the quantity of the released reporters present in the supernatant portion of the incubation mixture. If the reporter is capable of directly generating a detection signal (e.g., luminescent compounds, colored dyes, etc.), the presence or intensity of the detection signal may simply be determined qualitatively, quantitatively, or semi-quantitatively. For example, in one embodiment, the amount of enzyme is directly proportional to the signal intensity of the released reporters in the supernatant.

Typically, it is desired to assay the released reporters to determine the presence or intensity of a detection signal. This may be particularly useful in situations where the reporter is only indirectly detectable (e.g., a specific binding member). Alternatively, even if the reporter is directly detectable, a subsequent assay may still enhance the sensitivity and/or accuracy of detection. Any well-known assaying technique may be utilized to detect the reporters, including any of the techniques described above and/or shown in FIG. 1. For example, the first enzyme detection zone 31 of FIG. 1 may be capable of capturing the released reporters. Specifically, the first enzyme detection zone 31 may contain a receptive material having affinity for the reporter itself. In another embodiment, the first enzyme detection zone 31 may contain a receptive material that is capable of binding to binary complexes formed between the reporter and conjugated probes ("sandwich" assay format). In both cases, the amount of enzyme in the test sample is directly proportional to the signal intensity at the first enzyme detection zone 31.

Likewise, in still another embodiment, the first enzyme detection zone 31 may contain a receptive material that has a specific binding affinity for the reporter and conjugated probes, such that the reporter and conjugated probes compete for available binding sites ("direct competitive" assay format). Alternatively, the first enzyme detection zone 31 may contain a receptive material that has a specific binding affinity only for conjugated probes, and the reporter and receptive material compete for the binding sites of the conjugated probes ("indirect competitive" assay format). In both cases, the amount of enzyme in the test sample is inversely proportional to the signal intensity at the first enzyme detection zone 31. If desired, as discussed above, a second enzyme detection zone 35 may also be utilized. For example, in embodiments in which magnetic separation is employed, the second enzyme detection zone 35 may be capable of capturing any conjugated probes that do not bind to the first enzyme detection zone 31. Thus, in such embodiments, the amount of enzyme in the test sample is directly proportional to the signal intensity at the second enzyme detection zone 35.

In the embodiments described above, magnetic separation of the released magnetic substance, partially cleaved reactive complexes, and unreacted complexes, may occur prior to assaying the released reporters. In some embodiments, however, the magnetic separation step may be incorporated as part of the assaying procedure. For instance, referring again to FIG. 1, a magnetic device (not shown) may be positioned adjacent to the medium 23 at a location at or near (e.g., downstream) the point of application, e.g., the sample pad 22. Thus, when the incubation mixture flows through the medium 23, any magnetic substances (released magnetic substances, partially cleaved reactive complexes, and/or unreacted complexes) become immobilized within a separation zone. The magnetic device may also be positioned upstream from a point in which conjugated probes are optionally contacted with the released reporters (e.g., a conjugate pad). The reporters, having been separated from the magnetic substances, may then be assayed using detection zones 31 and/or 35 as described above.

The aforementioned detection techniques are described specifically in the context of enzymes. However, as stated, the present invention is equally suitable for detecting the presence or quantity of an enzyme inhibitor within a test sample. To detect the presence of an enzyme inhibitor within a test sample, a predetermined quantity of a corresponding enzyme may be mixed with the test sample and allowed to incubate. In the presence of a certain amount of an enzyme inhibitor, the enzyme-catalyzed reaction does not proceed at a detectable rate. Thus, the relationship between enzyme inhibitor concentration and signal intensity will be opposite to the relationship between enzyme concentration and signal intensity. As an illustration, an enzyme-catalyzed reaction will not occur in the presence of a certain amount of inhibitor. Thus, in one embodiment, all of the reactive complexes will be captured at the enzyme detection zone 31, which generates its maximum signal intensity. On the other hand, as the amount of enzyme inhibitor is reduced, the enzyme causes the reporters to release from the reactive complexes as described above. The signal intensity generated at the first enzyme detection zone 31 thus begins to decrease due to a corresponding decrease in the presence of released reporters. Likewise, the signal intensity generated at the second enzyme detection zone 35 may, in some embodiments, begin to increase due to a corresponding increase in the presence of released reporters. Accordingly, in this particular embodiment, the amount of enzyme inhibitor within the test sample is inversely proportional to the signal intensity at the first enzyme detection zone 31 and directly proportional to the signal intensity at the second enzyme detection zone 35.

II. Amine Detection

Amine detection may be accomplished in a variety of different ways. In one embodiment, for example, amine detection is accomplished in the present invention using a "chemichromic dye", i.e., a dye that exhibits a detectable color change upon chemical reaction with one or more functional groups. Without intending to be limited by theory, it is believed that the addition of an amino functional group ($NH_2$) to the chemichromic dye molecule induces either a shift of the absorption maxima towards the red end of the spectrum ("bathochromic shift") or towards the blue end of the spectrum ("hypsochromic shift"). The type of absorption shift depends on the nature of the dye molecule and on whether the amino group functions as an electron acceptor (oxidizing agent), in which a hypsochromic shift results, or whether the amino group functions as an electron donor (reducing agent), in which a bathochromic shift results. Regardless, the absorption shift provides a color difference that is detectable, either visually or through instrumentation, to indicate the presence of amines in the test sample. For example, prior to contact with an infected test sample, the chemichromic dye may be colorless or it may possess a certain color. However, after contacting the test sample and reacting with amines present therein, the dye exhibits a change in color that is different than its initial color. That is, the dye may change from a first color to a second color, from no color to a color, or from a color to no color.

Generally speaking, any chemichromic dye capable of exhibiting a detectable change in color upon reaction with an amine may be utilized in the present invention. Such dyes are generally well known to those skill in the art, and may be described, for instance, in U.S. Pat. Nos. 4,477,635 to Mitra; 5,837,429 to Nohr, et al.; 6,174,646 to Hirai, et al., which are incorporated herein in their entirety by reference thereto for all purposes. For example, one class of chemichromic dyes that is particularly useful in the present invention is arylmethane dyes, such as diarylmethanes, triarylmethanes, and so forth.

Triarylmethane dyes, for example, may have the following general structure:

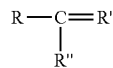

wherein R, R', and R" are independently selected from substituted and unsubstituted aryl groups, such as phenyl, naphthyl, anthracenyl, etc. The aryl groups may, for example, be substituted with functional groups, such as amino, hydroxyl, carbonyl, carboxyl, sulfonic, alkyl, and/or other known functional groups. When contacted with the dye, the amino group of the amine (e.g., ammonia, diamines, and/or tertiary amines) reacts with the central carbon atom of the dye. The addition of the amino group causes the dye to undergo a change in color. An example of the resulting structure is set forth below:

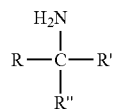

One particular example of a suitable triarylmethane dye is pararosanilin (also known as "basic fuchsin" or "magenta 0") and analogs thereof, such as rosanilin ("magenta I"), magenta II, new fuchsin ("magenta III"), methyl violet 2B, methyl violet 6B, methyl violet 10B ("crystal violet"), methyl green, ethyl green, acid fuchsin, and so forth. Pararosanilin shifts from a red color to colorless (i.e., white) upon reaction with an amine. Pararosanilin contains three phenylamine groups (i.e., amino-substituted aryl groups). Specifically, the structure of the structure of pararosanilin is set forth below:

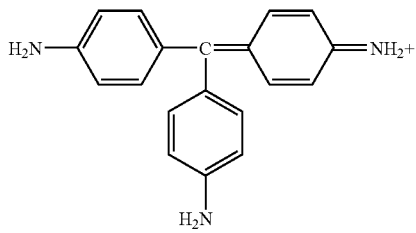

In some cases, triarylmethane dyes may be formed by converting a leuco base to a colorless carbinol and then treating the carbinol with an acid to oxidize the carbinol and form the dye. Thus, for example, pararosanilin may be derived by reacting the carbinol form of pararosanilin ("pararosaniline base") with an acid, such as, but not limited to, sulfonic acids, phosphoric acids, hydrochloric acid, and so forth. The carbinol form of pararosanilin is set forth below.

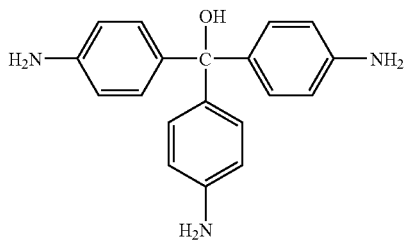

Another example of a suitable triarylmethane dye is alpha-naphtholbenzein and analogs thereof. Alpha-naphtholbenzein turns from an orange/red color to a gray/black color upon reaction with an amine. Alpha-naphtholbenzein contains a hydroxyl-substituted naphthyl group, a carbonyl-substituted naphthyl group, and a phenyl group. Specifically, the structure of alpha-naphtholbenzein is set forth below:

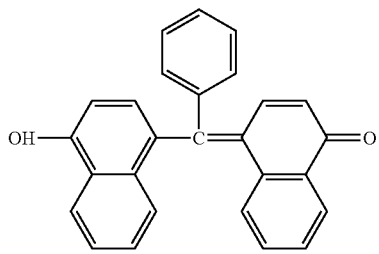

Still another example of a suitable triarylmethane dye is naphthocrome green and analogs thereof. Naphthocrome green turns from a pale yellow color to a blue/green color upon reaction with an amine. Similar to alpha-naphtholbenzein, naphthocrome green contains a hydroxyl-substituted naphthyl group, a carbonyl-substituted naphthyl group, and a phenyl group. However, each naphthyl group is also substituted with a sodium carboxyl. Specifically, the structure of naphthocrome green is set forth below:

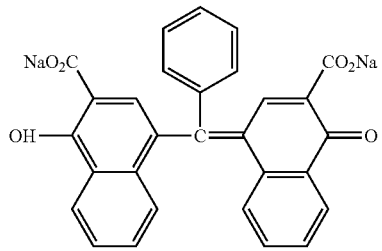

As indicated above, diarylmethanes may also be used in the present invention. One example of such a diarylmethane is 4,4'-bis(dimethylamino) benzhydrol (also known as "Michler's hydrol"), which has the following structure:

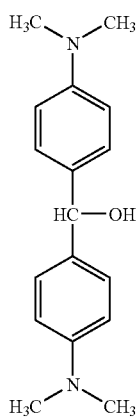

Still other examples include analogs of Michler's hydrol, such as Michler's hydrol leucobenzotriazole, Michler's hydrol leucomorpholine, Michler's hydrol leucobenzenesulfonamide, and so forth, as well as other diarylmethanes, such as malachite green leuco, malachite green carbinol, sodium 2,6-dichloroindophenolate, rhodamine lactam, crystal violet lactone, and crystal violet leuco.

Generally speaking, any of a variety of devices may be utilized that employ that amine detection techniques of the present invention. For example, in one embodiment, an assay device may be utilized that incorporates an amine detection zone. Referring again to FIG. 1, for instance, the chromatographic medium 23 may define an amine detection zone 61 within which is contained a chemichromic dye. The amine detection zone 61 may generally be located downstream or upstream from the first enzyme detection zone 31 and/or the second enzyme detection zone 35. In the illustrated embodiment, for example, the amine detection zone 61 is located downstream from both the first enzyme detection zone 31 and the second enzyme detection zone 33. Although not required, this particular configuration may help reduce the likelihood that any enzyme or enzyme inhibitors within the test sample inadvertently react with the chemichromic dye.

The dye may be applied to the chromatographic medium 23 in a variety of different ways. For example, the dye may be applied directly to the medium 23 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. The amount of the dye in the solution may range from about 0.001 to about 1 milligram per milliliter of solvent, and in some embodiments, from about 0.01 to about 0.1 milligrams per milliliter of solvent. The dye solution may be coated onto the chromatographic medium 23 using well-known techniques and then dried. The dye concentration may be selectively controlled to provide the desired level of detection sensitivity. Higher concentrations may provide a higher level of detection sensitivity when low amine levels are suspected. For example, as is well known in the art, the amount of the dye present within the amine detection zone 61 may be tailored to be equal to or in excess of the maximum amount of suspected amines within the test sample.

The chemichromic dye may be applied in a manner so that it does not substantially diffuse through the matrix of the chromatographic medium 23. This enables a user to readily detect the change in color that occurs upon reaction of the dye with an amine. For instance, the chemichromic dye may form an ionic and/or covalent bond with functional groups present on the surface of the chromatographic medium 23 so that it remains immobilized thereon. For example, in one embodiment, a positively-charged chemichromic dye may form an ionic bond with negatively-charged carboxyl groups present on the surface of some porous membranes (e.g., nitrocellulose). In other embodiments, the use of particles may facilitate the immobilization of the chemichromic dye at the amine detection zone 61. Namely, the dye may be coated onto particles, such as described above, which are then immobilized on the chromatographic medium 23. In this manner, the dye is able to readily contact a test sample flowing through the medium 23.

Although non-diffusive immobilizing techniques may be desired in some cases, it should also be understood that any other technique for applying the chemichromic dye to the chromatographic medium 23 may be used in the present invention. In fact, the aforementioned methods are only intended to be exemplary of the techniques that may be used in the present invention. For example, in some embodiments, certain components may be added to a chemichromic dye solution that substantially inhibit the diffusion of the dye into the matrix of the chromatographic medium 23. In other cases, immobilization may not be required, and the dye may instead diffuse into the matrix of the chromatographic medium 23 for reaction with the test sample.

The amine detection zone 61 may generally provide any number of distinct detection regions so that a user may better determine the concentration of an amine within the test sample. Each region may contain the chemichromic dye, or may contain different dyes for reacting with different types of amines. For example, the amine detection zone 61 may include two or more distinct detection regions (e.g., lines, dots, etc.). The detection regions may be disposed in the form of lines in a direction substantially perpendicular to the flow of the test sample through the chromatographic medium 23. Likewise, in some embodiments, the detection regions may be disposed in the form of lines in a direction substantially parallel to the flow of the test sample through the assay device.

III. Detection Techniques

After the assaying procedure, the first enzyme detection zone 31, the second enzyme detection zone 35, and/or the amine detection zone 61 may be analyzed, either qualitatively (e.g., visual observation), or semi-quantitatively or quantitatively (e.g., using instrumentation), for the presence or intensity of a respective signal. Depending on the nature of the reporters and the chemichromic dye utilized, the same or different detection techniques may be employed for the amine detection zone 61 as the enzyme detection zones 31 and/or 35. For example, reflectance techniques may be utilized for the amine detection zone 61 and enzyme detection zones 31 and/or 35 to quantitatively or semi-quantitatively determine color or color intensity. In one embodiment, color intensity of dyed reporters and a chemichromic dye may be measured as a function of absorbance, with an increased absorbance generally representing an increased amine concentration. For example, absorbance readings may be measured at a wavelength of 650 nanometers using a microplate reader from Dynex Technologies of Chantilly, Va. (Model # MRX). In still another embodiment, color intensity may be measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, $L^*$, $a^*$, and $b^*$, which correspond to three characteristics of a perceived color based on the opponent theory of color perception. The three variables have the following meaning:

$L^*$=Lightness, ranging from 0 to 100, where 0=dark and 100=light;

$a^*$=Red/green axis, ranging approximately from −100 to 100; positive values are reddish and negative values are greenish; and $b^*$=Yellow/blue axis, ranging approximately from −100 to 100; positive values are yellowish and negative values are bluish.

Because CIELAB color space is somewhat uniform, a single number may be calculated that represents the difference between two colors as perceived by a human. This difference is termed $\Delta E$ and calculated by taking the square root of the sum of the squares of the three differences ($\Delta L^*$, $\Delta a^*$, and $\Delta b^*$) between the two colors. In CIELAB color space, each $\Delta E$ unit is approximately equal to a "just noticeable" difference between two colors. CIELAB is therefore a good measure for an objective device-independent color specification system that may be used as a reference color space for the purpose of color management and expression of changes in color. Using this test, color intensities ($L^*$, $a^*$, and $b^*$) may thus be measured using, for instance, a handheld spectrophotometer from Minolta Co. Ltd. of Osaka, Japan (Model #CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still other suitable devices for measuring the intensity of a visual color may also be used in the present invention. For example, a suitable reflectance spectrophotometer or reader that may be used in the present invention is described in U.S. Patent App. Pub. No. 2003/0119202 to Kaylor, et al., which is incorporated herein in its entirety by reference thereto for all purposes.

In some cases, the detection techniques used for the amine detection zone 61 may be different than those used for the enzyme detection zones 31 and 35. For example, in one embodiment, the signal intensity of the enzyme detection zones 31 and 35 may be measured using fluorescence detection techniques. Fluorescence detection generally utilizes wavelength filtering to isolate the emission photons from the excitation photons, and a detector that registers emission photons and produces a recordable output, usually as an electrical signal or a photographic image. One suitable fluorescence detector for use with the present invention is a FluoroLog III Spectrofluorometer, which is sold by SPEX Industries, Inc. of Edison, N.J. Another example of a suitable fluorescence detector is described in U.S. Patent Application Publication No. 2004/0043502 to Song, et al., which is incorporated herein in its entirety by reference thereto for all purposes. Still other known detection techniques may also be utilized in the present invention for the first enzyme detection zone 31, the second enzyme detection zone 35, and/or the amine detection zone 61. For example, other suitable optical detection techniques may include, but not limited to, phosphorescence, diffraction, transmittance, etc. An optical reader may be capable of emitting light and also registering a detection signal (e.g., transmitted or reflected light, emitted fluorescence or phosphorescence, etc.).

Regardless of the manner in which the detection zones are analyzed, the result may be compared with a predetermined detection curve in which the signal (e.g., color or color intensity) of the first enzyme detection zone 31, the second enzyme detection zone 35, and/or the amine detection zone 61, is plotted versus various known concentrations of an enzyme, enzyme inhibitor, or amines. In this manner, the signal intensity may be measured and readily correlated to a certain concentration for providing quantitative or semi-quantitative results to a user.

Figure 3:
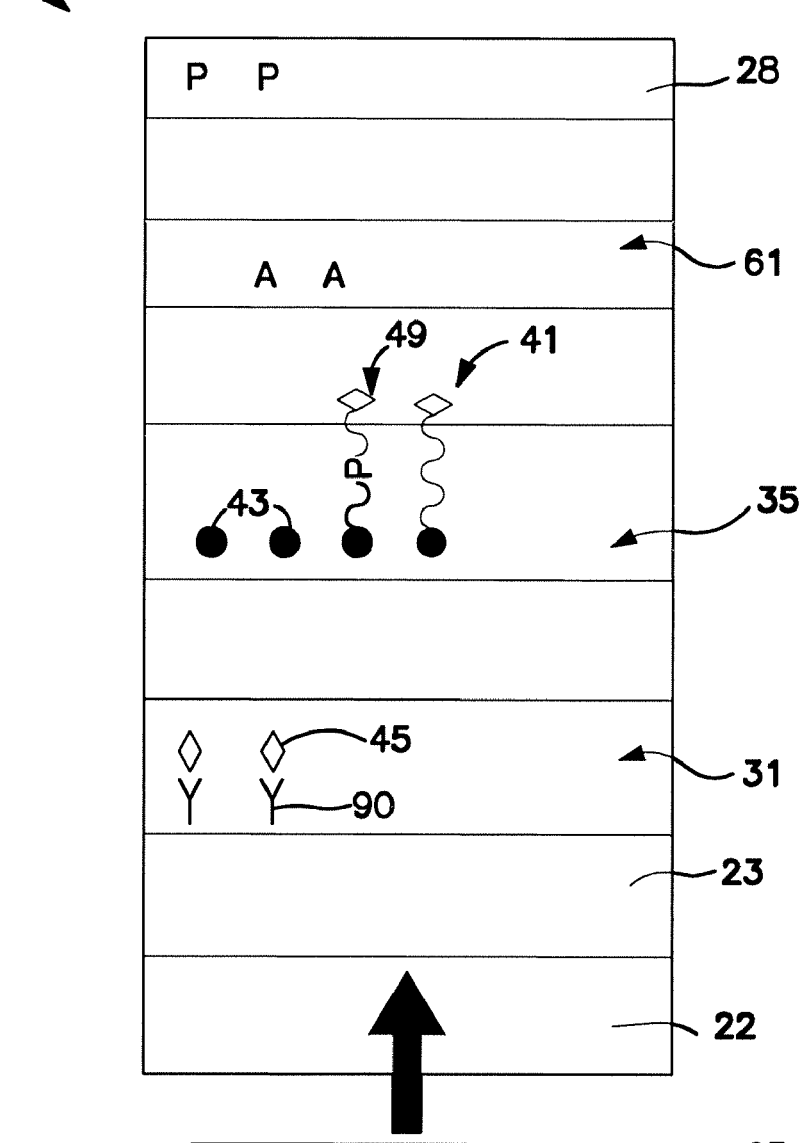
FIG. 3 is a schematic illustration of one assaying technique that may be used in one embodiment of the present invention to detect the presence or quantity of an amine and an enzyme (or enzyme inhibitor) within a test sample.

Referring to FIG. 3, one particular embodiment of a method for detecting the presence of a protease and amine will now be described in more detail. Initially, a test sample containing a protease P and amine A is mixed with reactive complexes 41 that each include a dyed particle 43 and specific binding member 45 (e.g., biotinylated substance) joined to a substrate 47 (e.g., protein or glycoprotein). The complexes 41 are allowed to incubate for a sufficient period of time to form an incubation mixture (designated numeral 65 in FIG. 3) that includes released dyed particles 43 and specific binding members 45, as well as an unreacted complex 41, partially cleaved complex 49, protease P, amine A, and any product (not shown) generated by the enzyme-catalyzed reaction. In some cases, the amine A may slightly inhibit the enzyme-catalyzed reaction; however, it is not believed that any such inhibition will have a significant affect on the accuracy of the assay.

The incubation mixture 65 is applied to the sample pad 22, as indicated by the illustrated directional arrow, and then travels to the first enzyme detection zone 31. Due to their smaller size, the released specific binding members 45 flow faster and have a higher probability of being captured by a first receptive material 90 within the first enzyme detection zone 31. The available binding sites in the first enzyme detection zone 31 may also be occupied by some of the unreacted complexes 41 and partially cleaved complexes 49. However, any unreacted complexes 41 and partially cleaved complexes 49 not captured by the first enzyme detection zone 31 travel to the second enzyme detection zone 35 and bind to a receptive material (not shown) contained therein. Because the released dyed particles 43 do not have an affinity for the first receptive material 90, they also travel to the second enzyme detection zone 35 and bind to a receptive material (not shown) contained therein. In addition, because the amines A have no specific affinity for the receptive materials within the first and second enzyme detection zones 31 and 35, they travel to the amine detection zone 61 where they react with the chemichromic dye (not shown). After the reaction, the amine detection zone 61 changes color in a manner that is detectable either visually or with instrumentation.

The present invention provides a relatively simple, compact and cost-efficient device for accurately detecting enzymes (or enzyme inhibitors) and/or amines within a test sample (e.g., vaginal fluid). In this manner, for example, vaginal fluid may be tested in a single step for the presence of amines and also for the presence of other diseases or disorders. The test result may be visible so that it is readily observed by the person performing the test in a prompt manner and under test conditions conducive to highly reliable and consistent test results. The device may then be discarded as a unit when the test is concluded. Such a single step detection technique has a variety of benefits. For example, as discussed above, the detection of amines within a vaginal fluid test sample may indicate the presence of certain types of vaginal infection (e.g., bacterial vaginosis or trichomonas vaginitis), while the detection of an enzyme or enzyme inhibitor within the test sample may indicate the presence of other types of vaginal infection (e.g., candidal vaginitis).

Besides diagnosing one or more types of infection in vaginal fluid, the method and diagnostic kit of the present invention may be used in any other application in which the detection of an enzyme, enzyme inhibitor, and/or amine may be desired. For example, many people (e.g., diabetics, burn victims, those suffering from suppressed immune systems, etc.) who have difficulty in healing and require extended periods for proper and complete wound healing are susceptible to infection. Bacteria and mold may also cause infection in hosts other than the human body, such as food. In many cases, these infections result in the formation of odorous amines and diamines, which may be produced by the metabolic processes of proteolytic bacteria together with short chain organic acids. Thus, as with vaginal infections, the ability to detect amines in other types contexts, such as in a wound exudate or food, may prove vastly beneficial. Likewise, the mere presence of an enzyme may, in some cases, indicate the existence of tissue or organ damage. Abnormal enzyme concentrations may also indicate other conditions, such as a bacterial or viral infection. For instance, the presence or concentration of an enzyme in a test sample may also serve as a diagnostic marker for some types of cancers and other conditions. As an example, prostate-specific antigen (PSA) is a well-known marker for prostate cancer. Other examples of diagnostic markers include cathepsin B (cancer), cathepsin G (emphysema, rheumatoid arthritis, inflammation), plasminogen activator (thrombosis, chronic inflammation, cancer), and urokinase (cancer).

The present invention may be better understood with reference to the following examples.

Example 1

β-casein was initially conjugated to dyed particles. Specifically, 2 milliliters of blue carboxylated particles (0.3-micrometer particle size, Bangs Laboratories, Inc. of Fisher, Ind.) were washed once with phosphate-buffered saline (PBS from Polysciences, Inc. of Warrington, Pa.) and then suspended in 1 milliliter of PBS. 36 milligrams of carbodiimide (Polysciences, Inc.) in 1 milliliter of PBS was added and the mixture was shaken for 30 minutes. The particles were washed twice with a borate buffer (Polysciences, Inc.), and then suspended in 1 milliliter of borate buffer. 1 milligram of β-casein (Sigma-Aldrich Chemical Co., Inc. of St. Louis, Mo.) was added and the mixture was shaken overnight at room temperature. The particles were washed once with the borate buffer and then re-suspended in 500 microliters of borate buffer. 1 milliliter of ethanolamine solution (0.1 molar, Polysciences Inc.) was added to the particles and shaken for 30 minutes. The particles were then washed four times with water and suspended in 2 milliliters of borate buffer.

Upon formation, the conjugated particles (hereinafter "BP-casein") were then biotinylated. Specifically, 4 milligrams of the BP-casein particles in 200 microliters of borate buffer were mixed with 1 milligram of EZ-Link® Sulfo-NHS-LC-Biotin (Pierce Biotechnology, Inc. of Rockford, Ill.) in 200 microliters of borate buffer. The mixture was shaken overnight and then washed five times with water. The washed particles were suspended in 1 milliliter of tris buffer (pH of 7.2, 20 millimolar). The biotinylated conjugated particles are hereinafter referred to as "BP-casein-B."

Example 2

The ability to form a membrane-based device for amine and/or enzyme assays was demonstrated. Initially, Millipore HF12002 porous nitrocellulose membranes were laminated onto corresponding supporting cards having a length of approximately 30 centimeters. Streptavidin (1.0 milligram per milliliter, Sigma-Aldrich Chemical Co., Inc.) was striped onto the membrane to form a first enzyme detection zone and Goldline™ (a polylysine solution obtained from British Biocell International) was striped onto the membrane (downstream from the first enzyme detection zone) to form a second enzyme detection zone. Alpha-naphtholbenzein (ANB) (5 milligrams per milliliter, Sigma-Aldrich Chemical Co., Inc.) was also striped onto the membrane (downstream from the enzyme detection zones) to form an amine detection zone. The membrane was dried for 1 hour at 37° C. A cellulosic fiber wicking pad (Millipore Co.) was attached to the end of the membrane closest to the amine detection zone. The assembled card was then cut into 4-millimeter wide devices. The resulting devices were sealed in a bag for storage.

Example 3

The ability to form a membrane-based device for amine and/or enzyme assays was demonstrated. Initially, Millipore HF12002 porous nitrocellulose membranes were laminated onto corresponding supporting cards having a length of approximately 30 centimeters. Anti-biotin antibody (2.0 milligrams per milliliter, Sigma-Aldrich Chemical Co., Inc.) was striped onto the membrane to form a first enzyme detection zone and Goldline™ (a polylysine solution obtained from British Biocell International) was striped onto the membrane (downstream from the first enzyme detection zone) to form a second enzyme detection zone. ANB dye (Sigma-Aldrich Chemical Co., Inc.) was also striped onto the membrane (downstream from the enzyme detection zones) to form an amine detection zone. The membrane was dried for 1 hour at 37° C. A cellulosic fiber wicking pad (Millipore Co.) was attached to the end of the membrane closest to the ANB dye zone. The assembled card was then cut into 4-millimeter wide devices. The resulting devices were sealed in a bag for storage.

Example 4

The ability to detect the presence of an enzyme and amine in accordance with the present invention was demonstrated. Four samples were tested. Each sample contained 13 microliters of the "BP-casein-B" of Example 1 (10 milligrams per milliliter); 100 microliters of Tween 20 (2%, Sigma-Aldrich Chemical Co., Inc.); and 300 microliters of tris buffer (pH of 7.4). Samples 1-4 contained cadaverine in an amount of 0.2, 0.0, 0.2, and 0.2 milligrams, respectively. Samples 1-4 also contained an active protease from *Bacillus polymyxa* (20 milligrams/milliliter), which is a metalloenzyme available from Sigma-Aldrich Chemical Co., Inc., in an amount of 0.5, 0.5, 0, and 0.05 micrograms, respectively. Sample 2 (the amine control) also contained 10 additional microliters of tris buffer (pH of 7.4), and Sample 3 (the enzyme control) contained 5 additional microliters of tris buffer (pH of 7.4). The samples were allowed to incubate for 10 minutes.

Each sample was then transferred to a well present on a microtiter plate. The assay device samples of Example 2 were then inserted into each respective well to initiate the test. After allowing the assay to develop for 10 minutes, the color intensity of each detection zone was observed. The qualitative results are set forth below in Table 1.

TABLE 1

Qualitative Color Results for Detection Zones

| Sample | First Enzyme Detection Zone | Second Enzyme Detection Zone | Amine Detection Zone |
|---|---|---|---|
| 1 | Weak | Strong | Gray |
| 2 | None | Strong | Yellow |
| 3 | Strong | None | Gray |
| 4 | Strong | Medium | Gray |

As indicated, the signal intensity exhibited by the first enzyme detection zone decreased in the presence of the enzyme, while the signal intensity exhibited by the second detection zone increased in the presence of the enzyme. The color of the amine detection zone changed from yellow to gray in the presence of the amine.

Example 5

The ability to detect the presence of an enzyme and amine in accordance with the present invention was demonstrated. Eight samples were tested. Each sample contained 25 microliters of the "BP-casein-B" of Example 1 (10 milligrams per milliliter); 600 microliters of Tween 20 (2%, Sigma-Aldrich Chemical Co., Inc.); and 900 microliters of Hepes buffer (pH of 7.2). Samples 1-8 contained cadaverine in an amount of 0.000 (amine control), 0.234, 0.468, 0.937, 1.875, 3.750, 7.500 and 15.000 micrograms per milliliter, respectively. Samples 1-8 also contained an active protease from *Bacillus polymyxa*, which is a metalloenzyme available from Sigma-Aldrich Chemical Co., Inc., in an amount of 0.0000 (enzyme control), 0.0275, 0.0550, 0.1100, 0.2200, 1.1000, 2.2000 and 11.0000 micrograms per milliliter, respectively. The samples were allowed to incubate for 10 minutes.

Each sample was then transferred to a well present on a microtiter plate. The assay device samples of Example 3 were then inserted into each respective well to initiate the test. After allowing the assay to develop for 10 minutes, the color intensity of each detection zone was observed. The qualitative results are set forth below in Table 2.

TABLE 2

Qualitative Color Results for Detection Zones

| Sample | First Enzyme Detection Zone | Second Enzyme Detection Zone | Amine Detection Zone |
|---|---|---|---|
| 1 | Strong | None | Yellow |
| 2 | Strong | None | Yellow |
| 3 | Strong | Weak | Yellow/Gray |
| 4 | Strong | Medium | Yellow/Gray |
| 5 | Medium | Medium | Yellow/gray |

TABLE 2-continued

Qualitative Color Results for Detection Zones

| Sample | First Enzyme Detection Zone | Second Enzyme Detection Zone | Amine Detection Zone |
|---|---|---|---|
| 6 | Medium | Strong | Yellow/gray |
| 7 | Weak | Strong | Gray |
| 8 | None | Strong | Gray |

As indicated, the signal intensity exhibited by the first enzyme detection zone decreased in the presence of the enzyme, while the signal intensity exhibited by the second enzyme detection zone increased in the presence of the enzyme. The color of the amine detection zone changed from yellow to gray in the presence of the amine.

Example 6

The ability to detect the presence of an enzyme and amine in accordance with the present invention was demonstrated. Six samples were tested. Each sample contained 50 micrograms of the "BP-casein-B" of Example 1; Tween 20 (2%, Sigma-Aldrich Chemical Co., Inc.); and 40 microliters of tris buffer (pH of 7.4). Samples 1-6 contained cadaverine in an amount of 0.00 (amine control), 0.30, 0.60, 1.25, 2.50 and 10.0 milligrams per milliliter, respectively. Samples 1-6 also contained an active protease from *Bacillus polymyxa*, which is a metalloenzyme available from Sigma-Aldrich Chemical Co., Inc., in an amount of 0, 1, 2, 4, 8 and 40 nanograms per milliliter, respectively. The samples were allowed to incubate for 10 minutes.

Each sample was then transferred to a well present on a microtiter plate. The assay device samples of Example 2 were then inserted into each respective well to initiate the test. After allowing the assay to develop for 10 minutes, the reflectance intensity of each detection zone was measured using a reflectance reader. The quantitative results are set forth below in Table 3.

TABLE 3

Quantitative Color Intensity for Detection Zones

| Sample | Reflectance Intensity ($I_1$) of First Detection Zone | Reflectance Intensity ($I_2$) of Second Detection Zone | Amine Detection Zone |
|---|---|---|---|
| 1 | 2.0490 | 0.0263 | 0.2687 |
| 2 | 1.4070 | 0.6988 | 0.2890 |
| 3 | 1.1980 | 1.0920 | 0.2918 |
| 4 | 1.1080 | 1.3320 | 0.3169 |
| 5 | 0.8213 | 1.2800 | 0.3696 |
| 6 | 0.4298 | 1.2140 | 0.7020 |

As indicated, the signal intensity exhibited by the first enzyme detection zone decreased in the presence of the enzyme, while the signal intensity exhibited by the second enzyme detection zone increased in the presence of the enzyme. Also, the intensity of the amine detection zone increased in the presence of amine.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting an amine, enzyme, or enzyme inhibitor within a test sample, the method comprising:
    i) contacting an incubation mixture that comprises the test sample that may contain an amine, enzyme, or enzyme inhibitor and further comprises a plurality of reactive complexes that each comprises a substrate joined to a reporter and a specific binding member, said substrate being cleavable by a hydrolytic enzyme to release said reporter with a chromatographic medium, said chromatographic medium defining an enzyme detection zone within which is immobilized a receptive material that has an affinity for said specific binding member for generating an enzyme detection signal wherein the presence or quantity of a hydrolytic enzyme is determinable from said enzyme detection signal, and an amine detection zone positioned downstream from said enzyme detection zone, wherein a chemichromic dye is contained within said amine detection zone, said chemichromic dye being capable of undergoing a color change in the presence of an amine, wherein the presence or quantity of an amine is determinable from said color change;
    ii) determining the presence or quantity of an enzyme or enzyme inhibitor from said enzyme detection signal; and
    iii) determining the presence or quantity of an amine from said amine detection signal.

2. A method as defined in claim 1, wherein the quantity of an enzyme within the test sample is inversely proportional to the intensity of said enzyme detection signal.

3. A method as defined in claim 1, wherein the quantity of an enzyme within the test sample is directly proportional to the intensity of said enzyme detection signal.

4. A method as defined in claim 1, wherein said chromatographic medium further comprises a second enzyme detection zone within which a second enzyme detection signal is capable of being generated.

5. A method as defined in claim 4, wherein the quantity of an enzyme within the test sample is directly proportional to the intensity of said second enzyme detection signal.

6. A method as defined in claim 1, further comprising selectively controlling the pH level of the test sample to optimize the activity of an enzyme.

7. A method as defined in claim 1, wherein the test sample is obtained from vaginal fluid.

* * * * *